United States Patent
Cahill et al.

(10) Patent No.: US 11,918,187 B2
(45) Date of Patent: Mar. 5, 2024

(54) SYSTEMS AND DEVICES FOR AN ENDOSCOPE TUBELESS WORKING CHANNEL

(71) Applicant: Boston Scientific Scimed, Inc., Maple Grove, MN (US)

(72) Inventors: Ryan Cahill, Scituate, MA (US); Earl McAllister, Needham, MA (US); Alexander Joseph Burnham, Southbury, CT (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 938 days.

(21) Appl. No.: 16/874,861

(22) Filed: May 15, 2020

(65) Prior Publication Data

US 2020/0359879 A1 Nov. 19, 2020

Related U.S. Application Data (60) Provisional application No. 62/849,300, filed on May 17, 2019.

(51) Int. Cl.
*A61B 1/00* (2006.01)
*A61B 1/005* (2006.01)
(Continued)

(52) U.S. Cl.
CPC .......... *A61B 1/018* (2013.01); *A61B 1/00066* (2013.01); *A61B 1/00128* (2013.01); *A61B 1/0057* (2013.01); *A61B 1/008* (2013.01); *A61B 1/015* (2013.01); *A61B 1/05* (2013.01); *A61B 1/0676* (2013.01); *A61M 25/0032* (2013.01)

(58) Field of Classification Search
CPC ............ A61B 1/00066; A61B 1/00128; A61B 1/0057; A61B 1/008; A61B 1/015; A61B 1/05; A61B 1/0676; A61B 1/00105; A61B 1/0052; A61B 1/0055
See application file for complete search history.

(56) References Cited

U.S. PATENT DOCUMENTS 4,899,732 A * 2/1990 Cohen .................. A61B 1/0052
600/161
5,735,793 A * 4/1998 Takahashi .......... A61B 1/00128
600/153
(Continued)

FOREIGN PATENT DOCUMENTS

| EP | 1737335 A2 | 1/2007 |
|----|------------|--------|
| EP | 2508120 A1 | 10/2012 |
| WO | 2013106444 A1 | 7/2013 |

*Primary Examiner* — Timothy J Neal
(74) *Attorney, Agent, or Firm* — Bookoff McAndrews, PLLC (57) ABSTRACT

An endoscopic device has a handle including an adapter, a shaft connected to the handle, and one or more wires within the handle. The adapter defines one or more openings in a side or proximal end of the adapter. The shaft has a plurality of lumens extending from a proximal end of the shaft to a distal end of the shaft. A first lumen of the plurality of lumens is a working channel for receiving a medical instrument. Each of the one or more wires enter through the one or more openings in the adapter for guiding the one or more wires to a corresponding lumen other than the first lumen and to the distal end of the shaft.

20 Claims, 11 Drawing Sheets

(51) Int. Cl.
*A61B 1/008* (2006.01)
*A61B 1/015* (2006.01)
*A61B 1/018* (2006.01)
*A61B 1/05* (2006.01)
*A61B 1/06* (2006.01)
*A61M 25/00* (2006.01)

(56) References Cited

U.S. PATENT DOCUMENTS

| | | | | |
|---|---|---|---|---|
| 5,846,221 | A * | 12/1998 | Snoke | A61M 25/0136 604/533 |
| 2004/0138529 | A1* | 7/2004 | Wiltshire | A61B 1/0055 600/144 |
| 2005/0272975 | A1* | 12/2005 | McWeeney | A61M 25/0068 600/172 |
| 2006/0252992 | A1* | 11/2006 | Mitsumori | A61B 1/005 600/139 |
| 2007/0282167 | A1* | 12/2007 | Barenboym | A61B 1/0052 600/131 |
| 2012/0172667 | A1* | 7/2012 | Takeuchi | A61B 1/0055 600/140 |
| 2016/0174819 | A1 | 6/2016 | Ouyang et al. | |
| 2017/0143199 | A1 | 5/2017 | Grimmer | |
| 2017/0188793 | A1* | 7/2017 | Ouyang | A61B 1/015 |
| 2017/0332882 | A1 | 11/2017 | Yamamoto et al. | |

* cited by examiner

SYSTEMS AND DEVICES FOR AN ENDOSCOPE TUBELESS WORKING CHANNEL

CROSS-REFERENCE TO RELATED APPLICATIONS

This application claims the benefit of priority from U.S. Provisional Application No. 62/849,300, filed on May 17, 2019, which is incorporated by reference herein in its entirety.

TECHNICAL FIELD

The present disclosure relates generally to medical devices, including endoscopes. In particular, this disclosure is directed to systems and devices for a tubeless working channel in an endoscopic device.

BACKGROUND

Endoscopic devices typically have a handle and a shaft or insertion portion. The handle enables steering and physical manipulation of the shaft portion and may include controls for other operations of the device. A distal assembly may comprise part of the shaft portion and may have a plurality of channels or lumens for endoscopic operation. Often, instruments or tools may be inserted in a working channel in the shaft portion for performing a therapeutic or diagnostic procedure. Therefore, a need exists for working channels with large cross-sectional areas to receive a variety of instruments and tools.

SUMMARY

According to an example, an endoscopic device has a handle including an adapter, a shaft connected to the handle, and one or more wires within the handle. The adapter defines one or more openings in a side or proximal end of the adapter. The shaft has a plurality of lumens extending from a proximal end of the shaft to a distal end of the shaft. A first lumen of the plurality of lumens is a working channel for receiving a medical instrument. Each of the one or more wires enter through the one or more openings in the adapter for guiding the one or more wires to a corresponding lumen other than the first lumen and to the distal end of the shaft.

A second lumen of the plurality of lumens is a lumen that receives wires for imaging and/or lighting. Lumens other than the first lumen and the second lumen are lumens each configured to receive an articulation wire for articulation of the device. The plurality of lumens comprise exactly four lumens.

A first wire of the one or more wires is for imaging and/or lighting. Wires other than the first wire are articulation wires for articulation of the device.

The adapter has a plurality of side openings and a proximal opening. A first side opening of the plurality of side openings is an opening that receives wires for imaging and/or lighting, and wherein other side openings other than the first side opening are openings each configured to receive an articulation wire for articulation of the device. The proximal opening is an opening configured to provide access to an instrument port and/or a suction port of the device.

The working channel does not have an inner tube disposed in the first lumen of the shaft. Walls defining the working channel at least partially define other of the plurality of lumens that receive the one or more wires. A cross-sectional area of the working channel has an area that is larger than a cross-sectional area of each of the other of the plurality of lumens. A cross-sectional shape of the working channel is non-circular.

An articulation joint is connected to the shaft and has a plurality of lumens extending from a proximal end of the articulation joint to a distal end of the articulation joint. A first lumen of the articulation joint is a working channel for the articulation joint for receiving the medical instrument. The working channel for the articulation joint has a same cross-sectional size and cross-sectional shape as the working channel for the shaft.

In another example, an endoscopic device has a handle, a shaft connected to the handle, and an articulation joint connected to the shaft. The shaft has a plurality of shaft lumens extending from a proximal end of the shaft to a distal end of the shaft. A first shaft lumen of the plurality of shaft lumens is a shaft working channel for receiving a medical instrument. Walls defining the shaft working channel at least partially define other of the plurality of shaft lumens. The articulation joint has a plurality of articulation joint lumens extending from a proximal end of the articulation joint to a distal end of the articulation joint. A first articulation joint lumen of the plurality of articulation joint lumens is a joint working channel for receiving the medical instrument. Walls defining the joint working channel at least partially define other of the plurality of articulation joint lumens.

A distal cap is connected to the articulation joint. The distal cap has a plurality of distal cap lumens extending from a proximal end of the distal cap to a distal end of the distal cap. A first distal cap lumen of the plurality of distal cap lumens is a cap working channel for receiving the medical instrument.

The shaft working channel is configured to interface with the joint working channel. The joint working channel is configured to interface with the cap working channel such that a working channel of the device extends from the distal cap to, and through, the shaft. Cross-sectional sizes of the shaft working channel, the joint working channel, and the cap working channel are substantially the same.

In another example, an endoscopic device has a handle including an adapter, a shaft connected to the handle, one or more wires within the handle, and a y-body connector attached to the proximal end of the adapter. The adapter defines one or more side openings in a side of the adapter and a proximal opening in a proximal end of the adapter. The shaft has a plurality of lumens extending from a proximal end of the shaft to a distal end of the shaft. A first lumen of the plurality of lumens is a working channel for receiving a medical instrument. The one or more wires enter through the one or more side openings in the adapter for guiding the one or more wires to a corresponding lumen, other than the first lumen, and to the distal end of the shaft. The y-body connector is configured to provide access from an instrument port of the handle to the working channel via the adapter.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to an operator and the term "distal" means a direction further from an operator. Although endoscopes are referenced herein, reference to endoscopes or endoscopy should not be construed as limiting the possible applications of the disclosed working channels and other aspects. For example, the disclosed aspects may be used with duodenoscopes, bronchoscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Clinical applications may benefit from endoscopic devices with large working channels. For example, suction/aspiration of viscous or non-newtonian liquids (such as the suction of mucus and clotted blood) may be more effective with endoscopic working channels that are large. Non-newtonian liquids may have higher flow rates with working channels that are large and that are non-circular. As another example, larger cross-sections of working channels may accommodate a greater variety of tools and instruments for therapeutic and diagnostic procedures. There may be other practical benefits for an endoscopic device with a larger working channel, such as improved device navigation, improved torque control, structural benefits to prevent or minimize kinks or damages to the device, etc. Therefore, aspects of the present disclosure are directed to endoscopic devices with tubeless working channels with large cross-sectional areas for optimal use.

Figure 1:
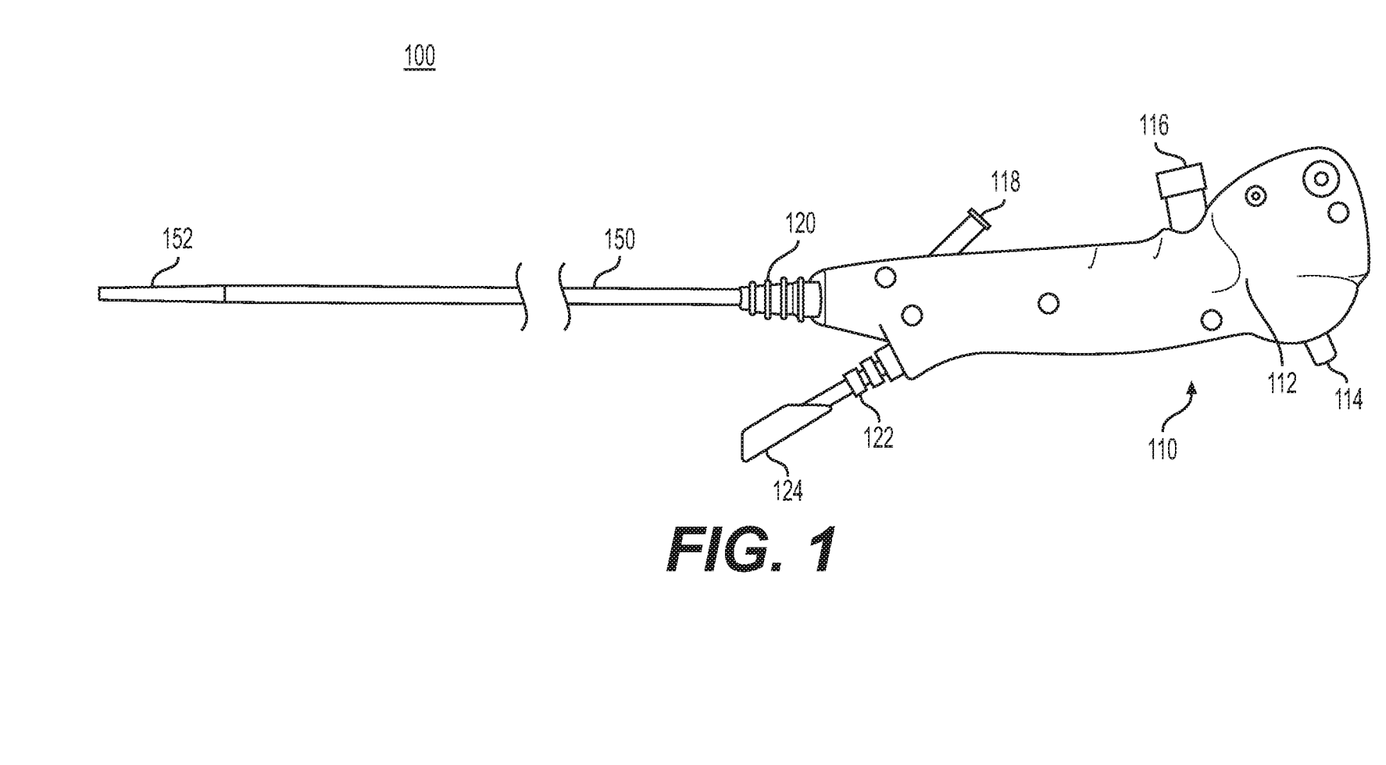
FIG. 1 depicts a side view of a medical device.

Reference is now made to FIG. 1. FIG. 1 depicts a medical device ("device") 100. The device 100 may be referred to herein as an endoscope, but it should be appreciated that the device 100 may be an endoscope, duodenoscope, bronchoscope, ureteroscope, colonoscope, catheter, or other type of medical device.

Device 100 includes a handle portion ("handle") 110 and a shaft/insertion portion ("shaft portion" or "shaft") 150. The handle 110 includes gripping surface 112, an articulation lever 114, a suction port 116, instrument/irrigation port ("instrument port") 118, a shaft strain relief portion 120, an umbilicus strain relief portion 122, and an umbilicus 124 (the proximal portion of which is shown in FIG. 1). At its distal end, the shaft 150 connects to a distal assembly 152.

The distal assembly 152 includes an articulation joint and a distal cap, both of which are not show in FIG. 1, but are described in connection with subsequent figures herein. The distal assembly 152 may include other devices or may be configured to receive other devices, such as a camera or light illuminating elements (e.g., light emitting diodes or "LEDs"). As described herein, the device 100 has a working channel that extends from the distal cap of the distal assembly 152, through the articulation joint and the shaft 150, to the instrument part 118 of the handle 110. The working channel of the device thus may be a combination of a working channel of the distal cap, a working channel of the articulation joint, and a working channel of the shaft 150, as described in detail herein.

The gripping surface 112 of the handle 110 enables physical handling of the device 100, e.g., by a medical professional or other operator. The articulation lever 114 is configured to be manipulated, and when the articulation lever 114 is manipulated by an operator, it articulates an articulation joint of the medical device 100 in an up/down direction (e.g., 180 degree articulation). The suction port 116 is a valve configured to provide air and/or water suction (e.g., through a working channel of the device 100). The instrument port 118 may be used for passing medical instruments or other tools and devices down the working channel of the device 100. In one example, as described by the techniques herein, the working channel of the device 100 may be a tubeless working channel (e.g., an open channel without an additional tube inserted for guiding an inserted tool). The working channel has a large cross-sectional area for receiving medical instruments and other tools and devices.

The shaft strain relief 120 is configured to interface with the shaft 150 of the device 100. The umbilicus 124 is connected to the umbilicus strain relief portion 122 and is configured to extend from the handle 110 for connection to an external device (e.g., a controller, computing device, processor and/or display device not shown in FIG. 1). For example, the umbilicus 124 may be used to connect the device 100 to components to provide optical controls of the device 100, including camera, video, light, etc. The shaft 150 is configured to be inserted into a patient for medical treatment (e.g., via one or more orifices of a patient's body).

Figure 2:
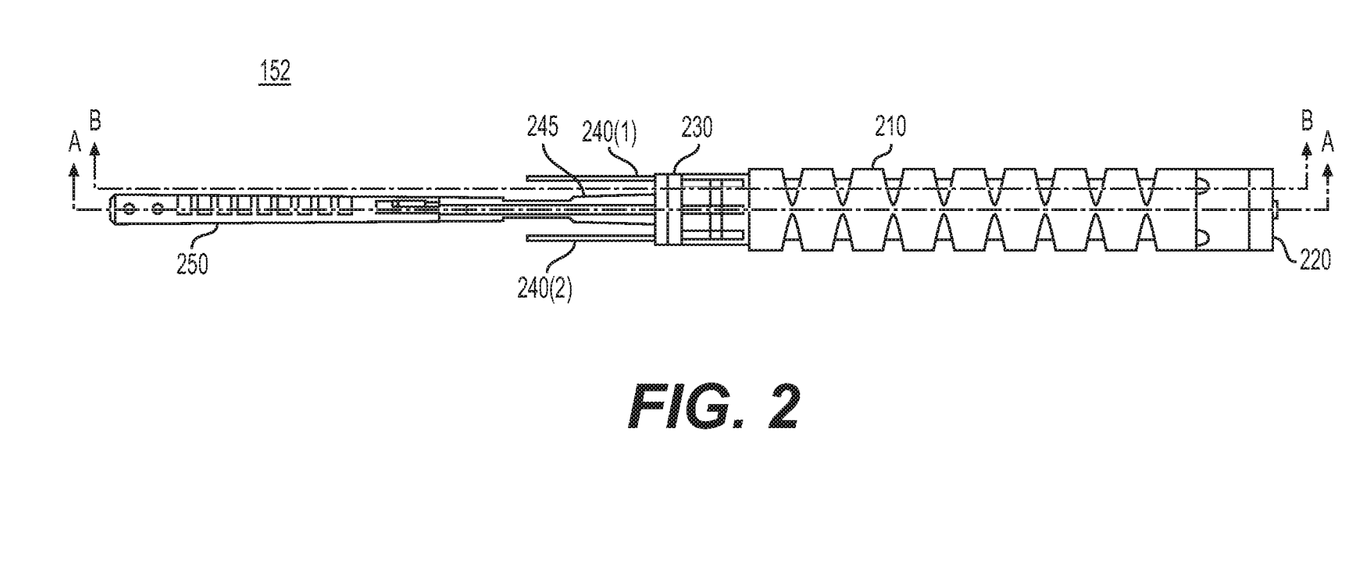
FIG. 2 depicts a side view of a distal assembly portion and electronics of the medical device.

Reference is now made to FIG. 2, which depicts a side view of the distal assembly 152 and certain electronics that extend through shaft 150 and umbilicus 124. The distal assembly 152 comprises an articulation joint 210, distal cap 220, a plurality of cables and wires 245, e.g., for connections to a camera and LEDs, a Bowden disk 230, and two articulation wires 240(1) and 240(2). The cables and wires 245 within distal assembly 152 extend through shaft 150 and umbilicus 124 to a circuit board 250. Circuit board 250 may be at an end of umbilicus 124 that connects to the external controller. Alternatively, the circuit board 250 may be in the handle 110. Thus, the circuit board 250 is not part of the distal assembly 152 itself, but is configured for connections to the LED wires and the camera cables disposed through the distal assembly 152.

In general, the articulation joint 210 is configured with multiple lumens. These lumens may operate as a tubeless working channel for the articulation joint 210, lumen(s) to receive the articulation wires 240(1) and 240(2), and lumen(s) to receive wires for the LEDs/camera. Similarly, the shaft 150 resides between handle 110 and distal assembly 152 and is configured with multiple lumens that may operate as a tubeless working channel for the shaft 150, lumen(s) to receive articulation wires 240(1) and 240(2), and lumen(s) to receive wires for the LEDs/camera. The articulation joint 210 and the shaft 150 are described in more detail in subsequent figures herein.

The distal cap 220 of the distal assembly 152 includes a camera and two LEDs. Further details of the distal cap 220 are provided in connection with FIGS. 3A and 3B below. The distal cap 220 is attached to a distal end of the articulation joint 210. A cable for the camera, as well as two sets of one or more wires for each of the respective LEDs may pass through the distal cap 220 and the articulation joint 210. The camera cable may include multiple wires that are held together by a wire harness. The Bowden disk 230 is attached to the proximal end of the articulation joint 210. The articulation wires 240(1) and 240(2) extend from the handle 110 (not shown in FIG. 2) through the shaft 150 and the articulation joint 210 for controlling movement of the articulation joint 210 in an up or down direction.

Figure 3A:
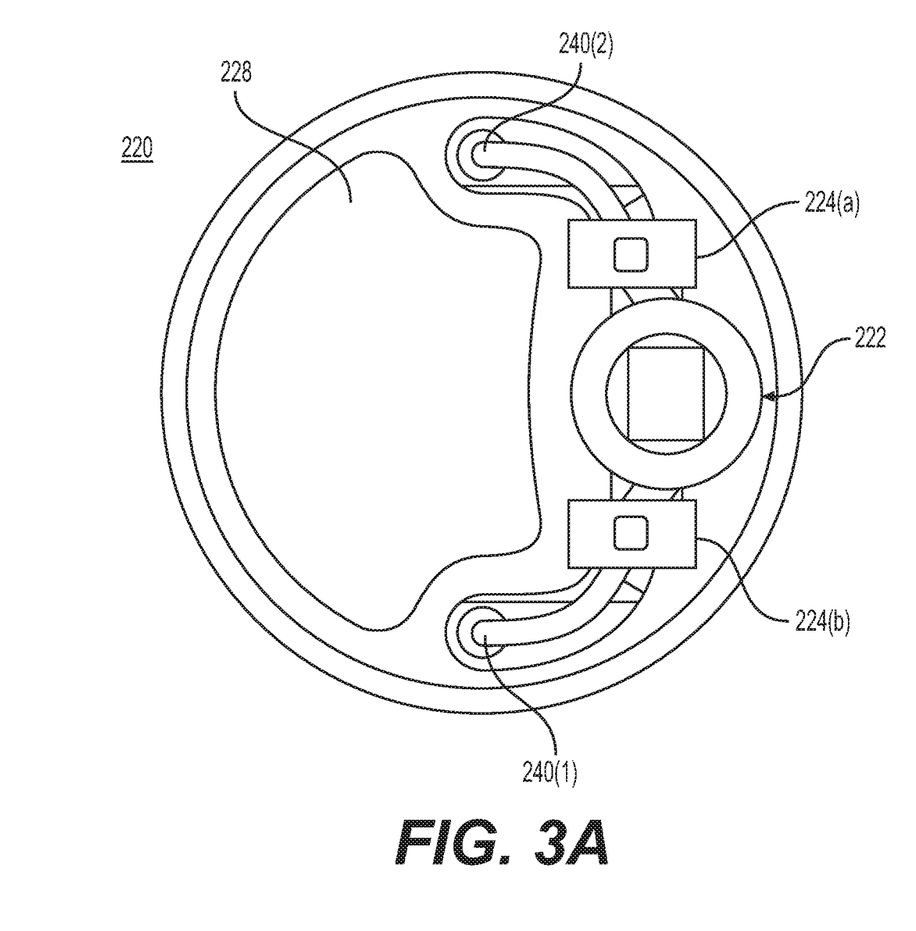
FIGS. 3A and 3B show an end view and a perspective view, respectively, of a distal cap of the distal assembly.

Reference is now made to FIG. 3A, which depicts an end view of the distal cap 220. As shown in FIG. 3A, the distal cap 220 includes a camera 222, two LEDs 224(a) and 224(b) on opposite sides of camera 222, articulation wires 240(1) and 240(2), and an opening 228 (e.g., an opening for a tubeless working channel). It should be appreciated that the articulation wires 240(1) and 240(2) are two separate wires, though they are shown in FIG. 3A as forming a continuous loop.

Figure 3B:
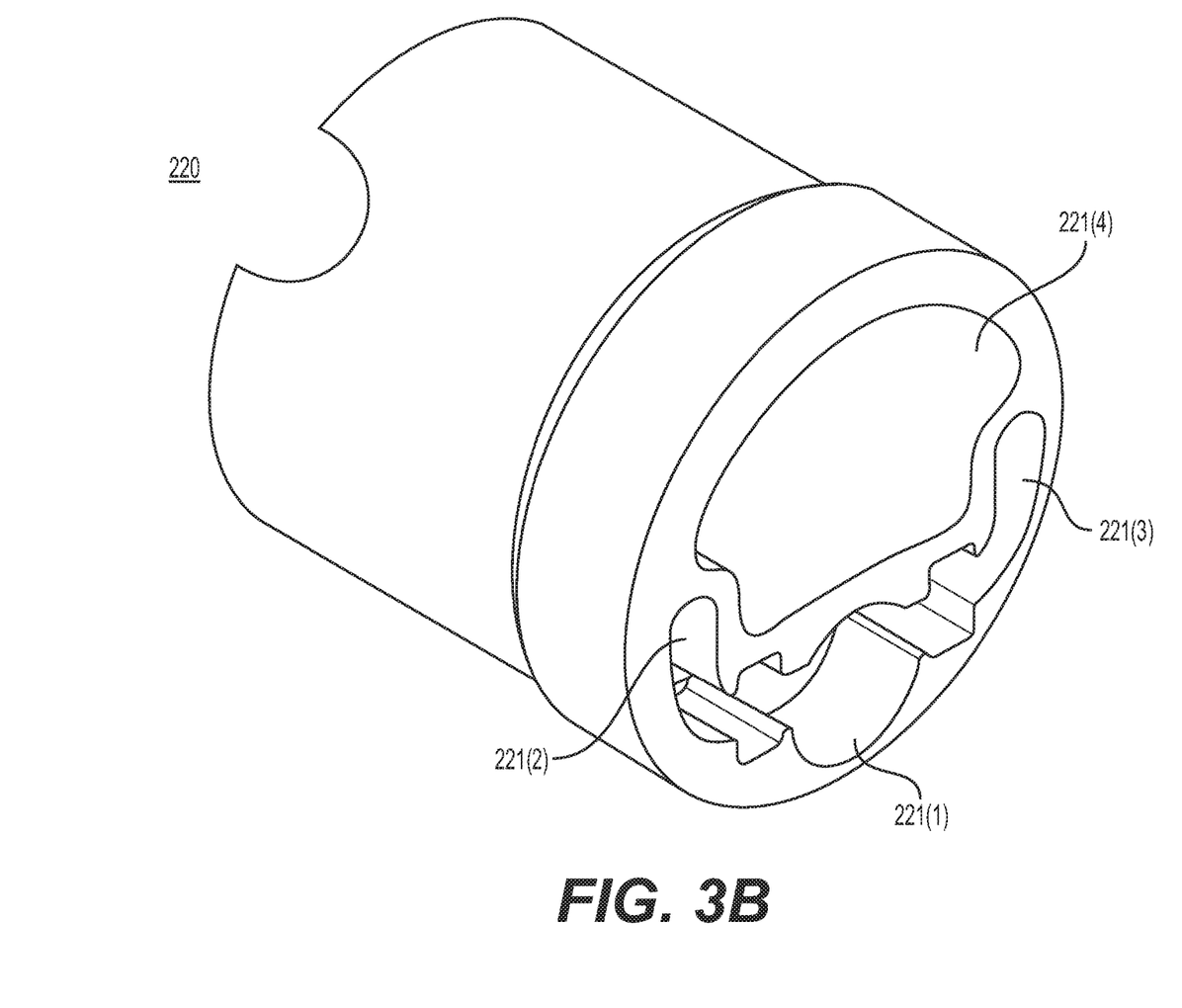

Reference is now made to FIG. 3B, which shows a perspective view of the distal cap 220 without camera 222, LEDs 224(a), 224(b), and wires 240(1), 240(2). The distal cap 220 has four lumens, shown at reference numerals 221(1)-221(4) in FIG. 3B. The camera 222 and LEDs 224(a) and 224(b) may reside in a first lumen (e.g., lumen 221(1)), the articulation wire 240(1) may reside in a second lumen (e.g., lumen 221(2)), the articulation wire 240(2) may reside in a third lumen (e.g., lumen 221(3)), and a fourth lumen (e.g., lumen 221(4)) may be utilized for a tubeless working channel of the distal cap 220. As described herein, the working channel of the distal cap 220 may interface with the working channel of the articulation joint 210 and the working channel of the shaft 150 to comprise the working channel of the device 100. Lumens 221(1), 221(2), and 221(3) may be separate or, as shown in FIG. 3B, in communication.

A reflective paint may be applied to either an inner wall of the distal cap lumen in which the LEDs reside (lumen 221(1)) or outside of a camera barrel. The reflective paint may be used to focus light emitted from the LEDs and/or to increase the amount of light that exits the distal cap 220. The LEDs 224(a) and 224(b) are configured to be angled toward the camera 222, for example, to provide the camera 222 with sufficient lighting for observation by a medical professional or operator of the device 100. The LEDs 224(a) and 224(b) may reside in a lumen, such as lumen 221(1).

Figure 4A:
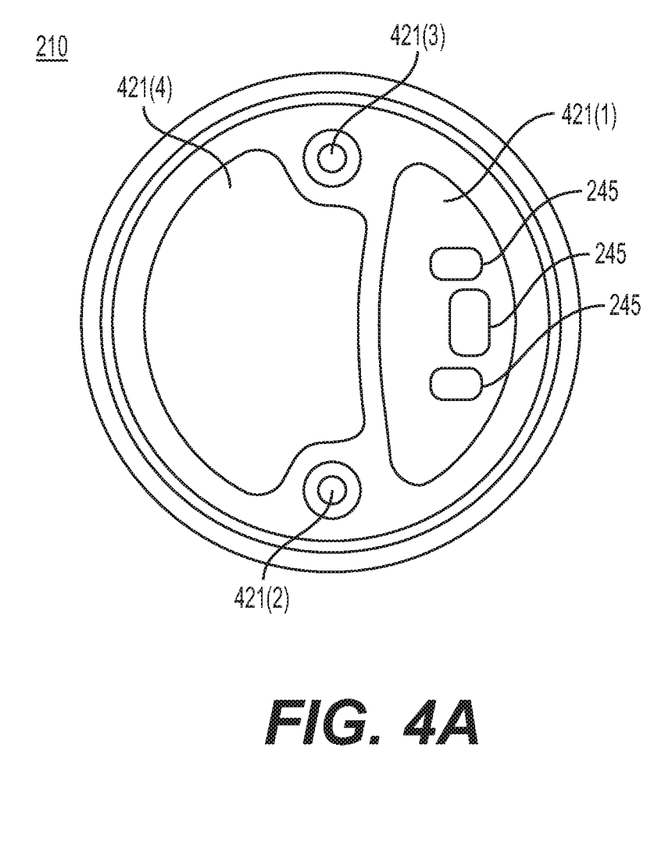
FIGS. 4A and 4B show a cross-sectional view and a perspective view, respectively, of an articulation joint of the distal assembly.

Reference is now made to FIG. 4A, which shows a cross-sectional view of the articulation joint 210. The articulation joint 210 is part of the distal assembly 152. The articulation joint 210 has four lumens 421(1)-421(4) that are similar in function to lumens 221(1)-221(4) described in connection with FIG. 3B, above. For example, lumen 421(1) of the articulation joint 210 is similar in function to lumen 221(1) of the distal cap 220 in that lumen 421(1) is configured to hold wires and cables 245 for connection to the camera 222 and the LEDs 224(a) and 224(b) (described in connection with FIG. 3A, above). In one example, lumen 421(1) holds a wire for each of the LEDs 224(a) and 224(b) and one cable for the camera 222 (e.g, the cable may comprise multiple wires for the camera 222 that are held together with the wires for LEDs 224(a) and 224(b) using a wire harness). Lumen 421(2) of the articulation joint 210 is similar in function to lumen 221(2) of the distal cap 220 and holds articulation wire 240(1) to connect with an articulation lever, and lumen 421(3) of the articulation joint 210 is similar in function to lumen 221(3) of the distal cap and holds articulation wire 240(2) to connect with the articulation lever. The articulation lever of the handle is configured to adjust the articulation wires 240(1) and 240(2) for up/down articulation. For example, moving the articulation lever in one direction pulls on one articulation wire to move in the "up" direction, and moving the articulation lever in another direction pulls on another articulation wire to move in the "down" direction.

Lumen 421(4) of the articulation joint 210 is utilized as the working channel for the articulation joint 210. The working channel of the articulation joint 210 is part of the working channel for the device (together with the working channel for the distal cap 220 and the working channel for the shaft 150, described in more detail herein).

Figure 4B:
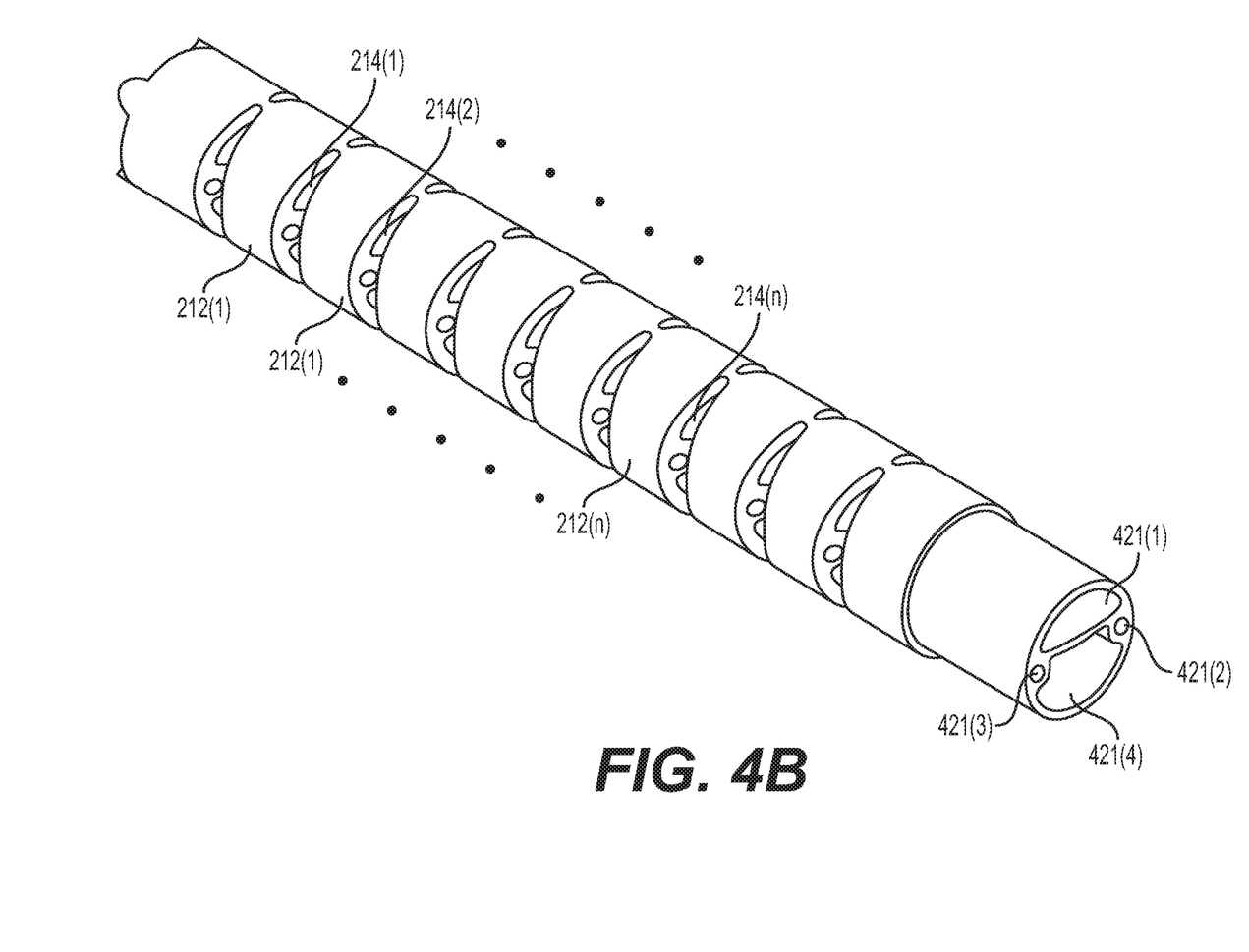

FIG. 4B shows a perspective view of the articulation joint 210. FIG. 4B shows the articulation joint without any wires passing through the lumens 221(1)-221(4). The articulation joint 210 shown in FIG. 4B is a single-piece that is formed of injection-molded polypropylene. The thickness of the outer walls of the articulation joint tapers so as to provide greater strength at a proximal end of the articulation joint (e.g., the wall is thinner at the distal end). The articulation joint 210 includes multiple links, shown at reference numerals 212(1)-212(n). The links 212(1)-212(n) are connected by hinge portions 214(1)-214(n). The articulation joint 210 may be encased with a thin polyurethane cover.

Figure 5:
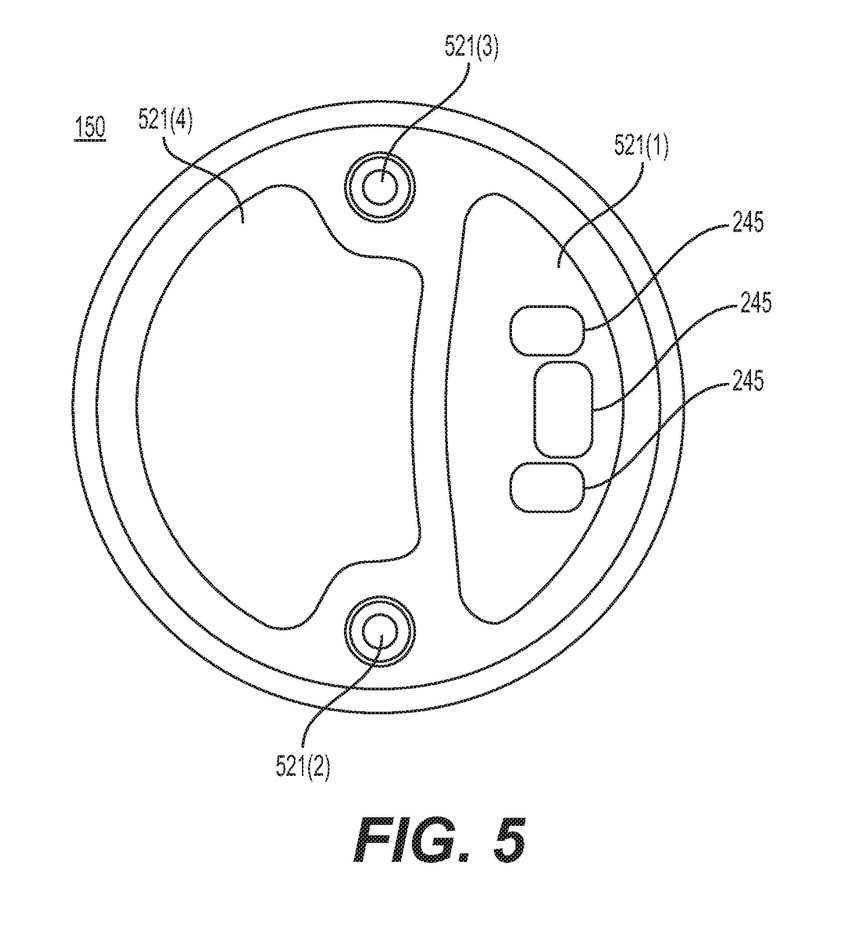
FIG. 5 shows a cross-sectional view of a shaft portion of the medical device.

Reference is now made to FIG. 5, which shows a cross-sectional view of the shaft 150 of the medical device 100. The shaft 150 has a braided extrusion as an outer layer. The shaft 150 has four lumens, shown at reference numerals 521(1)-521(4). The lumens 521(1)-521(4) are similar to lumens 221(1)-221(4) described in connection with the distal cap 220 and the lumens 421(1)-421(4) described in connection with the articulation joint 210. For example, lumen 521(1) of the shaft 150 is similar in function to lumen 221(1) of the distal cap 220 and lumen 421(1) of the articulation joint 210 in that lumen 521(1) is configured to hold wires and cables 245 for connection to the camera 222 and LEDs 224(a) and 224(b). Lumen 521(2) of the shaft 150 is similar in function to lumen 221(2) of the distal cap 220 and lumen 421(2) of the articulation joint 210 and holds articulation wire 240(1) to connect with the articulation lever. Lumen 521(3) of the shaft 150 is similar in function to lumen 221(3) of the distal cap and lumen 421(3) of the articulation joint 210 and holds articulation wire 240(2) to connect with the articulation lever. Lumen 521(4) of the shaft 150 is utilized as the working channel for the shaft 150. The working channel for the shaft 150, together with the working channel of the articulation joint 210 (e.g., lumen 421(4)) and the working channel of the distal cap 220 (e.g., lumen 221(4)) comprise the working channel for the device 100. In one example, the distal end of lumen 521(4) of the shaft 150 interfaces with the proximal end of lumen 421(4) of the articulation joint 210, and the distal end of lumen 421(4) of the articulation joint 210 interfaces with the proximal end of lumen 221(4) of the distal cap 220. Thus, the working channel of the device 100 extends from the distal cap 220 to, and through, the shaft 150 (e.g., the combination of lumens 221(4), 421(4), and 521(4)). Similarly, lumens 221(1), 421(1), and 521(1) interface together, lumens 221(2), 421(2), and 521(2) interface together, and lumens 221(3), 421(3), and 521(3) interface together to form corresponding channels from the distal cap 220 to, and through, the shaft 150.

As shown in FIGS. 3A, 4A and 5, lumen 221(4), lumen 421(4), and lumen 521(4) each has a significantly large cross-section area for the working channel of the device 100 compared to traditional endoscopic working channels. For example, lumen 221(4), lumen 421(4), and lumen 521(4) (and thus the working channel for the shaft 150 and the device 100) each has a cross-sectional area that is a significantly high percentage of the respective cross-sectional areas for the distal cap 220, the articulation joint 210, and the shaft 150. In some examples, the working channel for the shaft 150 may have different cross-sectional areas for different sizes of the shaft 150. In a first example, for smaller shaft sizes, the cross-sectional area of the working channel may be 2.16 millimenters (mm)$^2$, when the cross-sectional area of the shaft 150 may be 11.35 mm$^2$, and thus, the working channel cross-sectional area in this example may comprise 19% of the shaft cross-sectional area. In a second example, for medium shaft sizes, the cross-sectional area of the working channel may be 6.03 mm$^2$, while the cross-sectional area of the shaft 150 may be 19.63 mm$^2$, and thus, the working channel cross-sectional area in this example may comprise 30.7% of the shaft cross-sectional area. In a third example, for large shaft sizes, the cross-sectional area of the working channel may be 8.62 mm$^2$, while the cross-sectional area of the shaft 150 may be 26.42 mm$^2$, and thus, the working channel cross-sectional area in this example may comprise 32.6% of the shaft cross-sectional area. It should be appreciated that these measurements are merely examples, and may be within tolerances of +/−10%. In one example, the working channel cross-sectional area may comprise 50% or more of the shaft cross-sectional area. These cross-sectional measurements for the working channel are larger than working channels for traditional endoscopic devices, and the large cross-sectional area for the working channel of the device may be accomplished due to a lack of an independent tube (e.g., inner tube within a lumen) that typically comprises working channels in traditional endoscopic devices.

For example, a typical endoscopic device may have a tube with a circular cross-section disposed in a lumen and may extend from the distal cap to the handle. In these traditional endoscopic devices, the tube may operate as a working channel for instruments or tools. The present disclosure, in contrast, describes a working channel that utilizes the entire cavity of lumens 221(4), 421(4), and 521(4), together, as the working channel for the device 100 without an inner tube residing in any one or more of the lumens 221(4), 421(4) and 521(4). Thus, the working channel for the device 100 is tubeless in that it does not contain a separate inner tube disposed in the lumens 221(4), 421(4), and/or 521(4) as the working channel, but rather, the entire cavity of the lumens 221(4), 421(4), and 521(4) may be utilized as the working channel for instruments and other tools. Accordingly, the working channel of the device 100 (and individually, the working channel for the distal cap 220, the articulation joint 120, and the shaft 150) in the present disclosure has a cross-sectional area that is larger than typical working channel cross-sections for traditional endoscopic devices.

The significance of the design of the larger working channel relative to traditional endoscopic working channels is realized in clinical applications that benefit from larger working channels. Such applications include, for example, suction or aspiration of viscous or non-newtonian liquids. An example of a relevant application for the working channel with a large cross-sectional area is suction of mucus and clotted blood in lungs and airways.

Since an inner tube is not disposed within lumen 221(4), 421(4), and 521(4), the space within the distal cap 220, the articulation joint 210, and the shaft portion 150 that is not occupied by the camera cable, LEDs wires and articulation wires may be used as the working channel for the device 100 (e.g., a large, noncircular working channel). Thus, the distal cap 220, the articulation joint 210, and the shaft 150 each has four separated lumens to aid in the separation during the functional use of the device 100, which includes the passing of instruments via lumens 221(4), 421(4), and 521(4) in the working channel of the device 100 that would otherwise interfere with the wires and cables disposed in lumens 221(1)-221(3), 421(1)-421(3), and 521(1)-521(3).

As shown in FIGS. 3A, 4A, and 5, lumens 221(4), 421(4), and 521(4), respectively, may have a cross-sectional shape that is noncircular. Thus the working channel of the device 100 may have a noncircular cross-sectional shape. In one example, lumens 221(4), 421(4), and 521(4) have a cross-sectional "sting-ray" or "clamshell" shape (and thus, the working channel of the device 100 may have these cross-sectional shapes). In one example, the walls of the working channel of the device may define, at least partially or fully, other of the lumens that receive the one or more wires. For example, the walls of lumens 221(4), 421(4), and 521(4) define the boundaries of the other lumens (e.g., lumens 221(1)-221(3), 421(1)-421(3), and/or 521(1)-521(3)).

Figure 6:
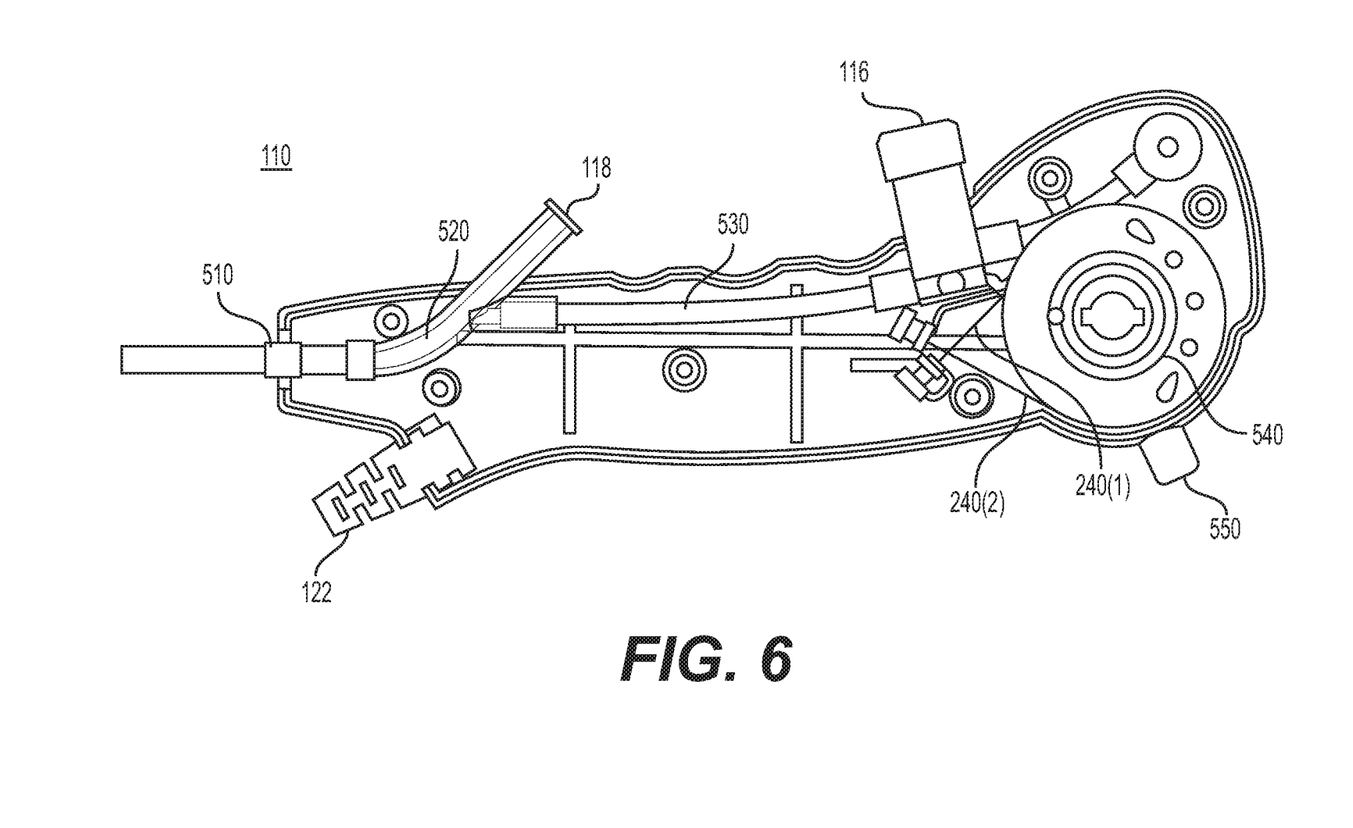
FIG. 6 shows a side cross-sectional view of a handle component of the medical device.

Reference is now made to FIG. 6, which shows a side cross-sectional view of the handle 110 for the device 100. The handle 110 cross-section shows suction port 116, instrument port 118, umbilicus strain relief 122, breakout adapter 510, a y-body connector 520, suction tube 530, cam wheel 540, thumb lever 550, and articulation wires 240(1) and 240(2). The breakout adapter 510 and y-body connector 520 are described further in connection with FIGS. 7A-7C herein. In general, the breakout adapter 510 is configured to route wires to appropriate lumens 521(1)-521(3) in the shaft 150, lumens 421(1)-421(3) in the articulation joint 210, and lumen 221(1)-221(3) in the distal cap 220. The suction port 116 is connected to the suction tube 530. The instrument port 118 is a valved port that can be used for irrigation and/or directing instruments in the endoscopic device 110 via, e.g., the working channel 228. For example, the instrument port 118 may connect with or allow access to the tubeless working channel 228 to allow for instrument and tool use. The cam wheel 540 is connected to the articulation wires 240(1) and 240(2). One of the articulation wires is used for upward articulation (e.g., articulation wire 240(1)) and another of the articulation wires is used for downward articulation (e.g., articulation wire 240(2)). The thumb lever is used to turn the cam wheel 540, which adjusts the articulation wires 240(1) and 240(2) for up/down articulation.

Figure 7A:
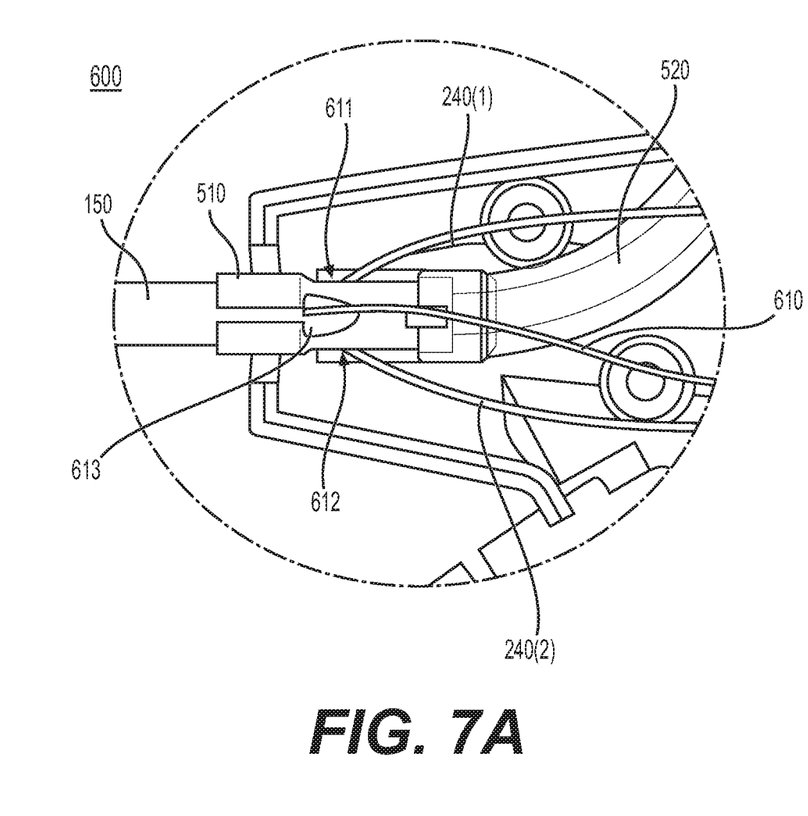
FIGS. 7A-7C shows a first side view, a second side view, and a perspective view, respectively, of a breakout adapter of the handle.

Reference is now made to FIG. 7A, which shows a first side view 600 of the breakout adapter 510 and the y-body connector 520. FIG. 7A shows a magnified portion of the handle 110 as it interfaces with the shaft 150. FIG. 7A shows the shaft portion 150, the breakout adapter 510, the y-connector 520, articulation wires 240(1) and 240(2) and wire harness (e.g., holding together LED wires and camera wires/cables) 610. The breakout adapter 510 connects at a proximal end with to the y-body connector 520 and to the shaft portion 150 at a distal end. The articulation wires 240(1) and 240(2) and wire harness 610 enter through side openings/channels ("openings") shown at reference numerals 611, 612, and 613 in the breakout adapter 510. As shown in FIG.

7A, side opening 611 is configured to receive articulation wire 240(1), side opening 612 is configured to receive articulation wire 240(2), and side opening 613 is configured to receive wire harness 610. In one example, the breakout adapter 510 is also referred to as a lumen breakout adapter for separating lumen channels of the shaft 150. The breakout adapter 510 also has a proximal opening (not shown in FIG. 7A). The proximal opening of the breakout adapter 150 interfaces with the y-body connector 520.

The breakout adapter 510 is configured to guide the articulation wires 240(1) and 240(2) and wire harness 610 into the appropriate lumen in the shaft 150. For example, the breakout adapter 510 guides the wire harness 610 to lumen 521(1) of the shaft via opening 613, guides articulation wire 240(1) to lumen 521(2) of the shaft 150 via opening 611, and guides the articulation wire 240(2) to lumen 521(3) of the shaft 150 via opening 612. Thus, the breakout adapter 510 separates the wiring of the device 100 (e.g., the electronic wiring and articulation wires) so that lumen 521(4) of the shaft 150, together with lumen 421(4) of the articulation joint 210 and lumen 221(4) of the distal cap 220, may be utilized as the working channel for the device 100. As a result, the working channel of the device 100 extends from the shaft 150 to the distal cap 220 without interference with the wires (e.g., the articulation wires 240(1) and 240(2) and the wire harness 610). The breakout adapter 510 enables tubeless working channel by appropriately guiding wires to the lumens that extend through the shaft portion 150.

The breakout adapter 510 is coupled to the handle 110 via a connection portion (not show in FIG. 7A). The breakout adapter 510 receives the wires at an appropriate one of the openings, and the wires are sealed in the appropriate openings with an adhesive placed around the wires and completely within the openings to close the openings. For example, breakout adapter 510 receives articulation wire 240(1) at opening 611, receives articulation wire 240(2) at opening 612, and receives wire harness 610 at opening 613. Subsequently, an adhesive is placed around articulation wire 240(1) at opening 611, around articulation wire 240(2) at opening 612, and around articulation wire 240(3) at opening 613 to close the openings and seal the lumens from the external environment. The Figures do not show the adhesive covering each of the openings of the adapter 510.

Figure 7B:
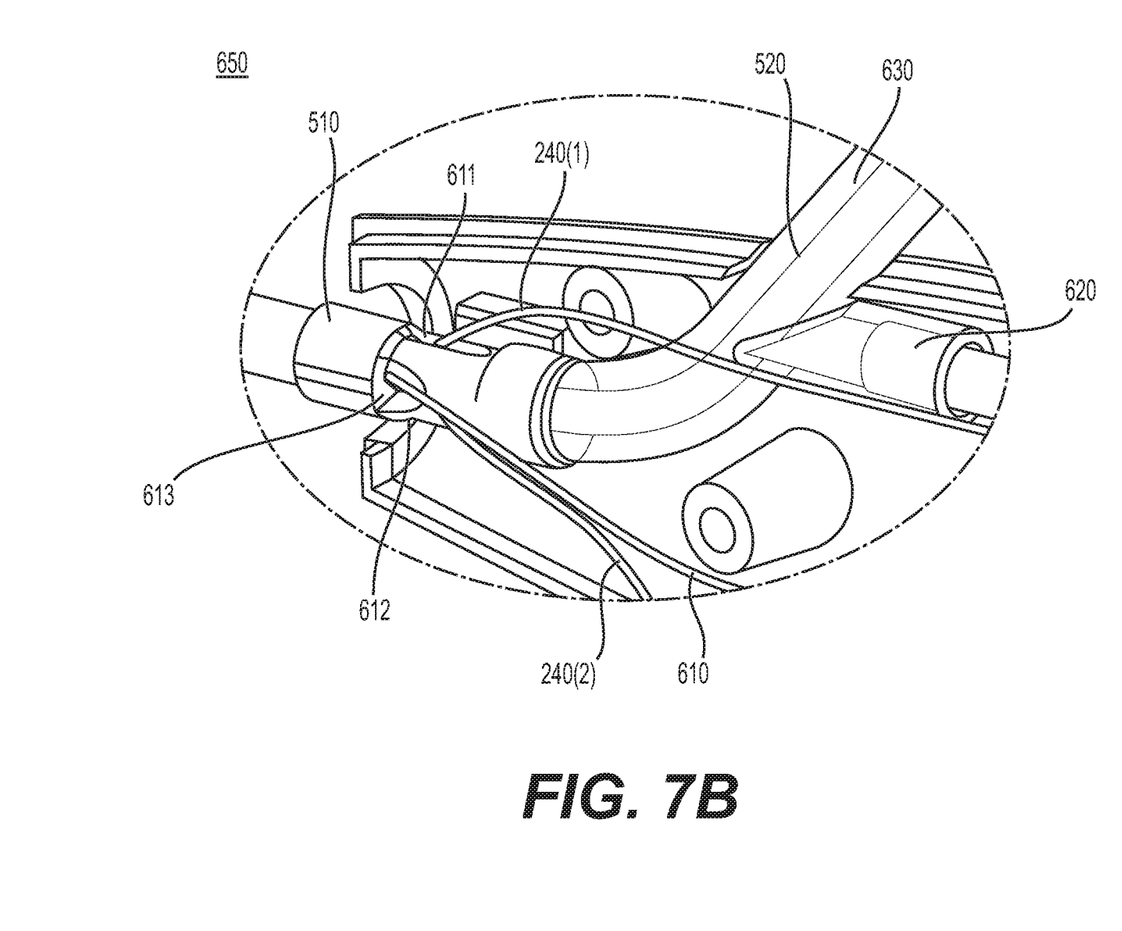

FIG. 7B shows a second side view 650 of the breakout adapter 510 and the y-body connector 520. As shown in FIG. 7B, articulation wire 240(1) is guided to a top opening 611 of the breakout adapter 510, articulation wire 240(2) is guided to a bottom opening 612 of the breakout adapter 510, and the wire harness 610 is guided to an opening 613 of the breakout adapter 510. Thus, as described in connection with FIG. 7A above, the breakout adapter 510 may appropriately guide the one or more wires to a corresponding lumen in the shaft 150 via the opening. As a result, the one or more wires are separated and do not interfere with one another or with the working channel of the device 100. As described in connection with FIG. 7A above, the breakout adapter 510 engages or couples to the handle 110 via a connection portion, and adhesive is placed on the breakout adapter 510 around the wires and the openings to close the openings and seal the lumens of the device 100.

As described in connection with FIG. 7A, above, breakout adapter 510 has a proximal opening (not shown in FIG. 7B) that interfaces with the y-body connector 520. The y-body connector 520 connects the proximal opening of the breakout adapter 510 to the suction port 116 via suction channel 620 shown in FIG. 7B. The y-body connector 520 also connects the proximal opening of the breakout adapter 510 to the instrument port 118 via channel 630. Thus, suction operations are able to be applied from the suction port 116 to distal end of the device 100 via the suction channel 620, the y-body connector 520, the proximal opening of the breakout adapter 510, the shaft 150, and the distal end 152. Similarly, the instrument port 118 may be used to guide instruments and/or tools to the working channel of the device via channel 630, y-body connector 520, the proximal opening of the breakout adapter 510, the working channel of the shaft 150, the working channel of the articulation joint 210 of the distal end 152, and the working channel of the distal cap 220.

Figure 7C:
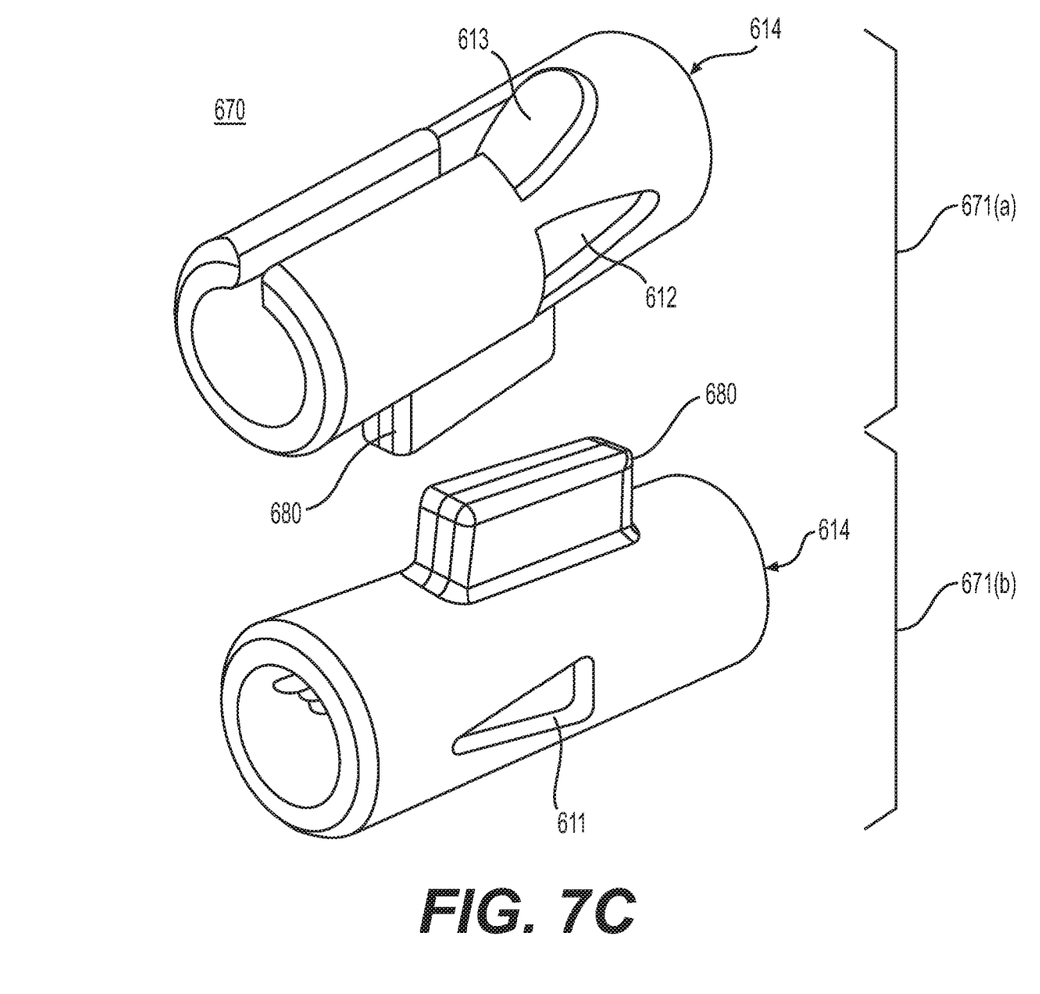

FIG. 7C shows a perspective views 670 of the breakout adapter 510. View 671(a) shows the opening 612 for receiving articulation wire 240(2) and opening 613 for receiving wire harness 610. View 671(a) also shows at reference numeral 614, the proximal opening of the breakout adapter 510. As described above in connection with FIGS. 7A and 7B, the proximal opening 614 of the breakout adapter 510 is configured to interface with or engage the y-body connector 520. View 671(a) shows a connection portion 680 that engages a receiving portion in the handle 110 to couple the breakout adapter 510 to the handle 110. For example, the connection portion 680 may engage or "plug into" a receiving portion of the handle 110 such that the breakout adapter 510 is coupled or attached to the handle 110. View 671(b) in FIG. 7C shows opening 611 for receiving the articulation wire 240(1), and the proximal opening 614.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical devices described herein may be using in combination with any other medical device known in the art, such as medical imaging systems or other scopes such as colonoscopes, bronchoscopes, ureteroscopes, duodenoscopes, etc., or other types of imagers.

It also should also be understood that one or more aspects of any of the medical devices described herein may be used for sensing, monitoring, or ablating tissue in any part of the human body. For example any of the medical devices described herein may be used in medical procedures such as for endoscopic cholangio-pancreatography, colonoscopies, cancer screening, examination of mucinous lesions, and/or other procedures where removal and/or detection of the type of tissue is needed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. An endoscopic device, comprising:
   a handle including an adapter, the adapter including a first opening on a proximal end of the adapter and a second opening on a side surface of the adapter, wherein the side surface extends between the proximal end of the adapter and a distal end of the adapter;
   a shaft connected to a distal end of the adapter, wherein the shaft includes a plurality of lumens extending from a proximal end of the shaft to a distal end of the shaft, wherein a first lumen of the plurality of lumens is a working channel for receiving a medical instrument; and a first articulation wire disposed in the handle, wherein the first articulation wire is configured to articulate a distal end of the endoscopic device in a first direction, wherein the first articulation wire extends through the second opening of the adapter to a second lumen of the shaft.

2. The endoscopic device of claim 1, wherein a third lumen of the plurality of lumens of the shaft is receives one or more r wires for imaging and/or lighting.

3. The endoscopic device of claim 2, wherein a fourth lumen of the plurality of lumens of the shaft is configured to receive a second articulation wire, wherein the second articulation wire is configured to articulate the endoscopic device in a second direction.

4. The endoscopic device of claim 3, wherein a first wall defining the second lumen forms a first concave portion of the working channel, and wherein a second wall defining the fourth lumen forms a second concave portion of the working channel.

5. The endoscopic device of claim 2, wherein a cross-sectional shape of each of the working channel and the third lumen is non-circular, wherein each of the working channel and the third lumen are closed lumens fully defined by the shaft, and wherein a first wall of the shaft defines portions of both of the working channel and the third lumen.

6. The endoscopic device of claim 5, wherein the first wall of the working channel is convex, and wherein a second wall, opposite the first wall, is concave.

7. The endoscopic device of claim 1, wherein the plurality of lumens of the shaft includes exactly four lumens.

8. The endoscopic device of claim 1, wherein the first opening is configured to provide access to an instrument port and a suction port of the endoscopic device.

9. The endoscopic device of claim 1, wherein a cross-sectional area of the working channel is larger than a cross-sectional area of each of the other lumens of the plurality of lumens.

10. The endoscopic device of claim 1, further comprising an articulation joint connected to the shaft and having a plurality of lumens extending from a proximal end of the articulation joint to a distal end of the articulation joint, wherein each lumen of the plurality of lumens of the articulation joint corresponds to a respective lumen of the plurality of lumens of the shaft.

11. The endoscopic device of claim 10, wherein the working channel is a shaft working channel, wherein a first lumen of the plurality of lumens of the articulation joint defines an articulation joint working channel, and wherein a cross-sectional size and a cross-sectional shape of the articulation joint working channel is the same as a cross-sectional size and a cross-sectional shape as the shaft working channel.

12. The endoscopic device of claim 1, wherein the adapter further includes a third opening and a fourth opening on the side of the adapter, wherein the third opening and the fourth opening are perpendicular to the second opening.

13. The endoscopic device of claim 12, wherein:
the first opening of the adapter corresponds to the working channel of the shaft,
the second opening of the adapter corresponds to the second lumen of the plurality of lumens of the shaft,
the third opening of the adapter corresponds to a third lumen of the plurality of lumens of the shaft, wherein one or more wires for imaging and/or lighting extend through the third opening of the adapter and into the third lumen, and
the fourth opening of the adapter corresponds to a fourth lumen of the plurality of lumens of the shaft, wherein a second wire extends through the fourth opening of the adapter and into the fourth lumen.

14. An endoscopic device, comprising:
a handle including an adapter, wherein the adapter includes:
a first opening on a proximal end of the adapter; and
a second opening on a side surface of the adapter, wherein the side surface extends between the proximal end of the adapter and a distal end of the adapter;
a shaft connected to the handle, wherein the shaft includes a first plurality of lumens extending from a proximal end of the shaft to a distal end of the shaft, wherein a first lumen of the first plurality of lumens is a first working channel configured for receiving a medical instrument, and wherein a first wall of the shaft defines (a) a first surface of the first working channel and (b) a second surface of a second lumen of the first plurality of lumens, and wherein a first portion of the first working channel defined by the first surface is concave, wherein a portion of the second lumen defined by the second surface is convex; and
an articulation joint connected to the shaft, wherein the articulation joint has a second plurality of lumens extending from a proximal end of the articulation joint to a distal end of the articulation joint, wherein a first lumen of the second plurality of lumens is a second working channel configured for receiving the medical instrument from the first working channel, and wherein one or more walls defining the second working channel at least partially define other lumens of the second plurality of lumens.

15. The endoscopic device of claim 14, further comprising a distal cap connected to the articulation joint, wherein the distal cap has a third plurality of lumens extending from a proximal end of the distal cap to a distal end of the distal cap, wherein a first lumen of the third plurality of lumens is a third working channel for receiving the medical instrument, wherein the third working channel of the cap has a same cross-sectional size and a same cross-sectional shape as both the first working channel of the shaft and the second working channel of the articulation joint.

16. The endoscopic device of claim 14, wherein the first plurality of lumens further includes a third lumen, and a fourth lumen,
wherein the first working channel of the shaft is opposite the third lumen of the first plurality of lumens,
wherein the second lumen of the first plurality of lumens is opposite the fourth lumen of the first plurality of lumens, and
wherein at least a portion of the working channel of the shaft is between the second lumen and the fourth lumen.

17. The endoscopic device of claim 14, wherein the adapter includes a third opening and a fourth opening, wherein each of the second opening, the third opening, and the fourth opening of the adapter is disposed on a cylindrical surface of the adapter.

18. The endoscopic device of claim 17, wherein the second opening of the adapter is opposite the third opening of the adapter.

19. An endoscopic device, comprising:
- a handle including an adapter, the adapter defining one or more side openings in a side surface of the adapter and a proximal opening in a proximal end of the adapter, wherein the side surface of the adapter extends between the proximal opening of the adapter and a distal opening of the adapter;
- a shaft connected to the handle and having a plurality of lumens extending from a proximal end of the shaft to a distal end of the shaft, wherein a first lumen of the plurality of lumens is a working channel for receiving a medical instrument;
- one or more wires disposed within the handle, wherein each of the one or more wires extends through the one or more side openings in the adapter for guiding the one or more wires to a corresponding lumen of the plurality of lumens of the shaft, other than the first lumen, and to the distal end of the shaft; and
- a y-body connector attached to the proximal end of the adapter.

20. The endoscopic device of claim 19, wherein the y-body connector is configured to provide access from an instrument port of the handle to the working channel of the shaft via the adapter.

* * * * *